US006989238B2

(12) United States Patent
Phelps

(10) Patent No.: US 6,989,238 B2
(45) Date of Patent: Jan. 24, 2006

(54) METHOD OF SORTING BIRDS

(75) Inventor: Patricia V. Phelps, Raleigh, NC (US)

(73) Assignee: Embrex, Inc., Research Triangle Park, NC (US)

( * ) Notice: Subject to any disclaimer, the term of this patent is extended or adjusted under 35 U.S.C. 154(b) by 0 days.

(21) Appl. No.: 10/301,245

(22) Filed: Nov. 21, 2002

(65) Prior Publication Data

US 2003/0096319 A1 May 22, 2003

Related U.S. Application Data

(63) Continuation of application No. 09/269,366, filed as application No. PCT/US97/18251 on Oct. 3, 1997, now Pat. No. 6,506,570.
(60) Provisional application No. 60/027,000, filed on Oct. 4, 1996.

(51) Int. Cl.
*G01N 33/53* (2006.01)
*C12N 15/12* (2006.01)

(52) U.S. Cl. .............................. 435/7.21; 435/7.1; 436/8
(58) Field of Classification Search ...................... 435/2, 435/4, 5, 6, 7, 7.21, 7.93, 9, 11, 28, 86, 287, 435/287.1, 287.2, 287.7, 287.8; 436/56, 94, 436/514, 568; 530/300, 350, 359, 367, 368, 530/389.1, 412, 827, 852, 853; 424/561; 536/24.3, 24.31

See application file for complete search history.

(56) References Cited

U.S. PATENT DOCUMENTS

| 5,508,165 | A | * | 4/1996 | Halverson et al. .............. 435/6 |
| 5,648,468 | A | * | 7/1997 | Spaulding .................... 530/359 |
| 5,679,513 | A |   | 10/1997 | Baker ............................. 435/6 |
| 5,679,514 | A |   | 10/1997 | Baker ............................. 435/6 |

FOREIGN PATENT DOCUMENTS

| EP | 0433084 | * | 6/1991 |
| EP | 0433084 A2 | | 6/1991 |
| FR | 2441378 | | 6/1980 |
| JP | 57136164 | | 7/1982 |
| JP | 63-216416 | | 9/1988 |
| JP | 4204238 | | 7/1992 |
| JP | 08-149982 | | 6/1996 |
| WO | WO 90/09188 | | 8/1990 |
| WO | WO 96/39505 | * | 6/1995 |
| WO | WO 95/23237 | | 8/1995 |
| WO | WO 98/14781 | * | 10/1996 |
| WO | WO 97/07399 | | 2/1997 |
| WO | WO 97/49806 | | 12/1997 |

OTHER PUBLICATIONS

Bercovitz et al. "Comparative sex–related differences of excretory sex steriods from day old andean condors vultur-gryphus and pregrine falcons falco–prergrinus non–invasive monitoring of neonatal endocrinlogy." Zoo Biology, vol. 7, No. 2, pp. 147–154.*

Weniger., Embryonic sex hormones in birds., Int. J. dev. Biology. 35–1–7 (1991).*

Weniger., Recherches sur la nature chimique des hormones sexuelles embryonnaires de poulet., Annales d'embryologie et de morphogenese., vol. 2, No. 4, pp. 433–444.*

Motelica–Heino; "Testosterone Concentrations in Chicken Gonads and Plasma during the Peri–etching Period," *Reprod. Fertil. Dev.* 7:1253–1260 (1995).

Clinton; "A rapid protocol for sexing chick embryos (*Gallus g. domesticus*)," *Animal Genetics* 25:361–362 (1994).

Guichard et al.; "Radioimmunoassay of Steriods Produced by Cultured Chick Embryonic Gonads: Differences according to Age, Sex, and Side," *General and Comparative Endocrinology* 32:255–265 (1977).

Guichard et al.; "Aspect comparatif de la synthèse de Stéroïdes sexuels par les gonads embryonnaires de Poulet à differents stades du développement (étude en culture organotypique à partir de précurseurs radioactifs)," General and Comparative Endocrinology 20:16–28 (1973). (Translation, summary only).

Motelica–Heino; "Testosterone Concentrations in Chicken Gonads and Plasma during the Peri–etching Period," *Reprod. Fertil. Dev.* 7:1253–1260 (1995).

Petitte et al.; "Sex Determination of Chick Embryos Using a W Chromosome–Specific Oligonucleotide Probe and PCR," *Proceedings of the XIX World's Poultry Conference, Amsterdam*, p. 531 (1992).

Stoll et al.; "The Existence of Sterolic Hormones In the Organism Of the Chicken Embryo During Its Sexual Differentiation," *Comptes Rendus Hebdomadaires Des Seances De L Academic Des Sciences* 242:9 1235–1237 (1956).

Tanabe et al.; "Ontogenetic Steroidogenesis by Testes, Ovary, and Adrenals of Embryonic and Postembryonic Chickens (*Gallus domesticus*)," *General and Comparative Endocrinology* 63:456–463 (1986).

(Continued)

*Primary Examiner*—Long V. Le
*Assistant Examiner*—Lisa V. Cook
(74) *Attorney, Agent, or Firm*—Myers Bigel Sibley & Sajovec, P.A.

(57) ABSTRACT

A method of determining the gender of a bird in ovo comprises detecting the presence or absence of an elevated level of a sex-related hormone in the extra-embryonic fluid of the bird egg, and then determining the gender of the bird within the egg from the presence of an elevated level of a sex-related hormone therein. In particular embodiments, the sex-related hormone is an estrogen. In other representative embodiments, the invention provides methods in which the extra-embryonic fluid is allantoic fluid. In other illustrative embodiments, the method can be carried out on chicken eggs prior to or during transfer of the eggs from incubator to hatcher.

18 Claims, No Drawings

OTHER PUBLICATIONS

Tanabe et al.; "Production and Secretion of Sex Steriod Hormones by the Testes, the Ovary, and the Adrenal Glands of Embryonic and Young Chickens (*Gallus domesticus*)," *General and Comparative Endocrinology* 39:26–33 (1979).

Teng et al.; "The Hormonal Regulation of Steroidogenesis and Adenosine 3':5'–Cyclic Monophosphate in Embryonic–Chick Ovary," *Biochem. J.* 162:123–134 (1977).

Woods; "Maturation of the Hypothalamo–Adenohypophyseal–Gonadal (HAG) Axes in the Chick Embryo" *The Journal of Experimental Zoology Supplement* 1:265–271 (1987).

Woods et al.; "Plasma Estrone Levels in the Chick Embryo," *Poultry Science* 61:1729–1733 (1982).

Weniger; "Research on the Chemical Nature of Embryonic Sex Hormones in Chicks," *Annals of Embryology and Morphogenesis* 2:4 433–444 (1969).

Gill et al.; "In Vivo Estrogen Synthesis by the Developing Chicken (*Gallus gallus*) Embryo[1]", General and Comparative Endocrinology, 49: 176–186, (1983).

Weniger; "Recherches sur la Nature Chimique des Hormones Sexuelles Embryonnaires de Poulot", Ann. Embryol. Morphog., 2: 433–444 (1969).

Weniger; "Embryonic Sex Hormones in Birds", Int. J. Dev. Biol., 35: 1–7 (1991).

Bendheim et al., "Hormonal Sexing Versus Surgicial Sexing in Birds," Proceedings of the First Conference of the European Committeee of the Association of Avian Veterinarians (Vienna), vol. 1, pp. 115–117 (1991).

Ozon; "Steroid Biosynthesis in Larval and Embryonic Gonads of Lower Vertebrae," *General and Comparative Endocrinology Supplement*, 2: 135–140 (1969).

Ozon; "Evidence of the steroid hormones, estrogens, in the blood of the adult chicken and in the chicken embryo," *Endocrinology*, 261: 5664–5666 (Dec., 1965). (French Language document and English Translation thereof).

* cited by examiner

METHOD OF SORTING BIRDS

RELATED APPLICATION INFORMATION

This application claims priority from and is a continuation of U.S. application Ser. No. 09/269,366, filed on Mar. 23, 1999, now U.S. Pat. No. 6,506,570, which claims priority under 35 U.S.C. § 371 from PCT Application No. PCT US97/18251, filed on Oct. 3, 1997, which claims priority from U.S. Provisional Application No. 60/027,000 filed on Oct. 4, 1996, the disclosures of which are incorporated by reference herein in their entireties.

FIELD OF THE INVENTION

The present invention relates to methods of sorting birds by gender, and particularly relates to such methods that can be carried out in ovo.

BACKGROUND OF THE INVENTION

Commercial birds are generally sorted by gender after hatch. Gender sorting is typically carried out by hand by visual inspection, and can be a time-consuming, tedious, and inaccurate process. Since the failure to properly sort birds by gender can lead to problems in poultry or egg production, it would be extremely useful to have a reliable means for sorting birds by gender without the need for visual inspection of the bird.

Accordingly, an object of the present invention is to provide a means for sorting birds by gender.

A further object of the present invention is to provide a means for sorting birds by gender that can be carried out without the need for visual inspection of the bird.

A still further object of the present invention is to provide a means for sorting birds by gender that can be carried out while the birds are in ovo.

SUMMARY OF THE INVENTION

The foregoing and other objects and aspects of the present invention may be accomplished by the method of determining the gender of a bird in ovo disclosed herein.

As a first aspect, the present invention provides a method of determining the gender of a bird in ovo, comprising the steps of: detecting the presence or absence of an elevated level of a sex-related hormone in the extra-embryonic fluid of a bird egg; and determining the gender of the bird within the egg from the presence of an elevated level of the sex-related hormone in the extra-embryonic fluid.

As a second aspect, the present invention provides a method of sorting a plurality of bird eggs by the gender of the birds in ovo therein, comprising the steps of: detecting the presence or absence of an elevated level of a sex-related hormone in the extra-embryonic fluid of each of the eggs; and then separating the plurality of eggs into a first subset of eggs having elevated levels of the sex-related hormone and a second subset of eggs not having elevated levels of the sex-related hormone, so that the first subset of eggs contains birds of one sex and the second subset of eggs contains birds of the other sex.

As a third aspect, the present invention provides a method of determining the gender of a bird in ovo, comprising the steps of: detecting the presence or absence of an elevated level of estrogen in the extra-embryonic fluid of a bird egg; and determining that the gender of the bird within the egg is a female from the presence of an elevated estrogen level in the extra-embryonic fluid.

Yet another aspect of the present invention is a method of sorting a plurality of bird eggs by the gender of the birds in ovo therein, comprising the steps of: detecting the presence or absence of an elevated estrogen level in the extra-embryonic fluid of each of the eggs; and then separating the plurality of eggs into a first subset of eggs having elevated estrogen levels and a second subset of eggs not having elevated estrogen levels, so that the first subset of eggs contains female birds and the second subset of eggs contains male birds.

These and other aspects of the present invention are described in more detail in the following description of the invention.

DETAILED DESCRIPTION OF THE INVENTION

Disclosed herein are methods of sorting birds by gender in ovo by detecting the presence or absence of an elevated level of a sex-related hormone in the extra-embryonic fluid of the egg. The phrase "sex-related hormone" as used herein, is any hormone that stimulates accessory sex structures and/or secondary sex characteristics in male or female birds. Exemplary sex-related hormones include estrogens and androgens. Alternately, a "sex-related hormone" is a hormone that is present at relatively high concentrations in birds of one gender and are present only at relatively low levels in birds of the other gender. For example, progestogens, which play a role in regulating the estrous cycle and maintaining pregnancy are also encompassed by the term "sex-related hormone". As a further alternative, "sex-related" hormones are those hormones that are characteristic of one of the sexes of birds and, thus, can be used to distinguish one sex from the other. The disclosed methods can be carried out by detecting the levels of more than one sex-related hormone. Generally, however, methods that involve detecting the presence or absence of elevated levels of one sex-related hormone are preferred.

Estrogens include, but are not limited to, estradiol, estradiol 17β, estriol and estrone. Also included are estrogen precursors, such as dihydroepiandrosterone, metabolic by-products of estrogen degradation, and naturally-occurring estrogen derivatives and variants. Androgens include, but are not limited to, testosterone and dihydrotestosterone. Also included are androgen precursors, such as androstenedione, androstenediol and androstanediol, metabolic by-products of androgen degradation, and naturally-occurring androgen derivatives and variants. Progestogens include, but are not limited to, progesterone and 17-OH progesterone. Also included are progesterone precursors, such as pregnenolone, metabolic by-products of progesterone degradation such as pregnanediol, and naturally-occurring progesterone derivatives and variants.

Preferred are methods of sorting birds by gender in ovo which involve detecting the presence or absence of an elevated level of estrogen in the extra-embryonic fluid of the egg. The presence of an elevated level of estrogen in the extra-embryonic fluids is indicative of a female bird. Any estrogen that is secreted into the extra-embryonic fluid in the egg may be used to carry out the present invention, with estradiol being preferred.

Those skilled in the art will appreciate that the inventive methods disclosed herein also encompass methods of sorting birds by detecting the presence or absence of an elevated level of a sex-related pheromone, protein or enzyme. Such pheromones, proteins or enzymes are present at relatively high concentrations in birds of one sex and at relatively low concentrations in birds of the opposite sex. Further, sex-related pheromones, proteins and enzymes can be used to distinguish one sex from the other.

To describe the present invention in an alternative way, the inventive methods disclosed herein provide a method of determining the sex of a bird in ovo, by measuring the level of a sex-related hormone in the extra-embryonic fluid of a bird egg and comparing that level to a predetermined standard, where a measurement above the standard indicates that the bird in ovo is of one sex, and a measurement below the standard indicates the bird in ovo is of the other sex. The predetermined standard will vary depending upon the species of bird being examined, the age of the egg at the time of examination, the acceptable percentage of error, and the hormone being examined. Experiments to determine a standard useful in a particular setting may be carried out using methods available in the art, and would be apparent to one skilled in the art (see, e.g., Examples 1–6 herein). In a preferred method, the eggs are chicken eggs, the hormone is estrogen, and the extra-embryonic fluid is allantoic fluid.

The terms "bird" and "avian" as used herein, are intended to include males or females of any avian species, but are primarily intended to encompass poultry which are commercially raised for eggs or meat. Accordingly, the terms "bird" and "avian" are particularly intended to encompass hens, cocks and drakes of chickens, turkeys, ducks, geese, quail and pheasant. Chickens and turkeys are preferred, with chickens being most preferred.

The term "in ovo," as used herein, refers to birds contained within an egg prior to hatch. The present invention may be practiced with any type of bird egg, including chicken, turkey, duck, goose, quail, and pheasant eggs. Chicken and turkey eggs are preferred, with chicken eggs most preferred.

Eggs sorted by the method of the present invention are fertile eggs which are preferably in the last half of incubation, more preferably in the third quarter of incubation. The detecting or sorting step may be carried out on chicken eggs on about the eleventh to nineteenth day of incubation, more preferably on about the thirteenth to seventeenth day of incubation, and most preferably on about the thirteenth to fifteenth day of incubation. The detecting step is preferably carried out on turkey eggs on about the fourteenth to twenty-sixth day of incubation, more preferably on about the sixteenth to twenty-first day of incubation, most preferably on about the sixteenth to nineteenth day of incubation. Those skilled in the art will appreciate that the present invention can be carried out at any predetermined time in ovo, as long as the level of a sex-related hormone in the extra-embryonic fluid at the chosen time is a reliable predictor of the sex of the bird.

According to the methods of sorting birds disclosed herein, the level of one or more sex-related hormones in the extra-embryonic fluid in the egg are measured, the level of the sex-related hormone being indicative of the sex of the bird. The extra-embryonic fluid can be from any source in the egg, including but not limited to allantoic fluid, amniotic fluid, yolk fluid, albumen fluid, or blood. There is no requirement that the fluid come from a single source—it may be advantageous to combine two or more of these fluids, e.g., to obtain sufficient volume on which to carry out analyses. Preferably, the extra-embryonic fluid is allantoic fluid.

While the methods of the present invention may be carried out on individual eggs, in a commercial setting the method is typically carried out on a plurality of eggs. In general, in a commercial setting, a plurality of eggs are incubated together in a common incubator. At about the beginning of the final quarter of incubation, the eggs are transferred from the incubator to a hatcher. This step is known as "transfer". The step of detecting the presence or absence of an elevated level of a sex-related hormone in the extra-embryonic fluid of each egg may be carried out prior to or after the transfer step. The detecting step can also be carried out at the time of transfer. Preferably, the detecting step is carried out prior to or at the time of the transfer of eggs from the incubator to the hatcher. Some methods of detecting the level of a sex-related hormone will cause a time delay while the diagnostic assays are being performed. According to this embodiment of the invention, after the hormone analyses are complete, it is preferable to sort and transfer the eggs to the hatcher at the same time.

The detecting step may be carried out by any suitable means which can detect differences in the levels of a sex-related hormone. The detection step may involve non-invasive techniques such as infrared spectroscopy analysis through the egg's shell or inner shell membranes or by inserting a biosensor into the appropriate target area (e.g., the allantoic sac if the target fluid is allantoic fluid), or by inserting a needle therein and withdrawing a fluid sample therefrom, which sample is subsequently subjected to an analysis such as by radioimmunoassay, infrared spectroscopy, photoacoustics, artificial nose techniques, or immunosensor techniques.

An "elevated" level of a sex-related hormone is a level that is at or above the normal range for an egg of the desired sex. For example, an "elevated" level of estrogen is a level that is at or above the normal range for an egg containing a female bird. Alternately, an elevated level of a sex-related hormone is a level that is sufficiently high to distinguish one gender of bird from the other in ovo, i.e., a level of estrogen that is sufficiently high to distinguish female from male birds. As a further alternative, an "elevated" level of sex-related hormone is a level at or above a predetermined level, such that the predetermined level can be used as a reliable predictor of sex in a bird in ovo. An "elevated" level of estrogen may be considered an estrogen level of 20, 40, 60, 80, or 100 picograms per milliliter or more in the target fluid. Likewise, an "elevated" level of a sex-related hormone may be considered a level of 20, 40, 60, 80, 100, or 200 picograms per milliliter or more in the target fluid.

After the detecting step, the plurality of eggs is then separated into a first subset of eggs having an elevated level of the sex-related hormone of interest, and a second subset of eggs not having elevated levels of the same sex-related hormone, so that said birds are sorted by gender. For example, if the indicator hormone is an estrogen, the first subset of eggs contains female birds and the second subset of eggs contains male birds. Where there is a time delay between withdrawing a sample from the eggs and obtaining the results of the diagnostic test, the eggs can simply be marked with a label, wax pencil, or other indicia or other suitable marking means that corresponds to an indicia associated with the sample withdrawn, and the eggs subsequently sorted when the results from the diagnostic tests are available.

After separating the eggs into a first and second subset, the eggs are separately incubated to hatch. This step may be conveniently carried out by simply placing the eggs in separate hatchers.

The present invention is explained in greater detail in the following non-limiting examples.

EXAMPLES 1–6

Allantoic and amniotic fluids were sampled from either Day 11 or Day 17 chicken embryos. The Day 17 embryos were then necropsied and the sex determined by visual observation of the gonads. Blood samples were collected from the Day 11 embryos, frozen and set aside for PCR analysis for the W specific chromosome to determine embryonic sex. The samples were then subjected to a radioimrunoassay (Coat-A-Count Estradiol kit, Diagnostic Products Corporation) to determine the amount of estradiol therein. The results are presented in Table 1.

TABLE 1

| Embryo Age | Fluid | Sex | Estradiol (pg/ml) |
|---|---|---|---|
| 17 | allantois | F | 260 |
|  |  |  | 414 |
|  |  |  | 266 |
| 17 | allantois | M | UD |
|  |  |  | UD |
|  |  |  | 15 |
| 17 | amnion | F | 4 |
|  |  |  | 17 |
|  |  |  | 11 |
| 17 | amnion | M | UD |
|  |  |  | 9 |
|  |  |  | UD |
| 11 | allantois | TBD | 24 |
|  |  |  | 69 |
|  |  |  | UD |
|  |  |  | 12 |
|  |  |  | UD |
|  |  |  | UD |
|  |  |  | UD |
|  |  |  | 27 |
| 11 | amnion | TBD | UD |
|  |  |  | UD |
|  |  |  | UD |
|  |  |  | UD |
|  |  |  | UD |
|  |  |  | UD |

UD = Undetectable
TBD = To Be Determined

The foregoing examples are illustrative of the present invention, and are not to be construed as limiting thereof. The invention is defined by the following claims, with equivalents of the claims to be included therein.

That which is claimed is:

1. A method of determining the gender of a bird in ovo, comprising the steps of:
   providing a bird egg containing an embryo and allantoic fluid;
   detecting the presence or absence of estrogen in the allantoic fluid;
   determining the presence or absence of an elevated level of estrogen in the allantoic fluid in ovo by comparison with a predetermined standard; and
   predicting that the gender of the bird embryo in ovo is a female from the presence of an elevated estrogen level in said allantoic fluid in ovo.

2. A method according to claim 1, wherein said determining step is carried out by a method selected from the group consisting of radioimmunoassay, infrared spectroscopy, artificial nose analysis, photoacoustics, and immunosensor analysis.

3. A method according to claim 1, wherein said detecting step is carried out during the last half of embryonic development.

4. A method according to claim 1, wherein said egg is a chicken egg.

5. A method according to claim 4, wherein said detecting step is carried out from day 11 to day 19 of embryonic development.

6. A method according to claim 4, wherein said detecting step is carried out from day 13 to day 17 of embryonic development.

7. A method according to claim 1, wherein said determining step is carried out on a sample of allantoic fluid removed from the bird egg.

8. A method according to claim 1, wherein a biosensor is inserted into the allantoic fluid of the bird egg in ovo, and said determining step is carried out in situ within the bird egg.

9. A method according to claim 1, wherein an elevated level of estrogen is a level of 20 picograms per milliliter or greater in said allantoic fluid in ovo.

10. A method according to claim 9, wherein an elevated level of estrogen is a level of 40 picograms per milliliter or greater in said allantoic fluid in ovo.

11. A method according to claim 10, wherein an elevated level of estrogen is a level of 80 picograms per milliliter or greater in said allantoic fluid in ovo.

12. A method according to claim 1, wherein said estrogen is selected from the group consisting of estradiol, estriol, estrone or a combination thereof.

13. A method of sorting a plurality of bird eggs by the gender of the bird embryos in ovo therein, comprising the steps of:
   providing a plurality of bird eggs each containing an embryo and allantoic fluid;
   detecting the presence or absence of estrogen in the allantoic fluid of each egg;
   determining the presence or absence of an elevated estrogen level in the allantoic fluid of each of said eggs by comparison with a predetermined standard; and then
   separating said plurality of eggs into a first subset of eggs having elevated estrogen levels and a second subset of eggs not having elevated estrogen levels, so that said first subset of eggs are predicted to contain female embryos and said second subset of eggs are predicted to contain male embryos.

14. A method according to claim 13, further comprising the step of incubating said eggs together in a common incubator prior to said detecting step.

15. A method according to claim 13, wherein said separating step is followed by the step of separately incubating said first subset of eggs and said second subset of eggs to hatch.

16. A method according to claim 13, further comprising the step of transferring said eggs to a hatcher after said determining step.

17. A method according to claim 13, wherein said determining step is carried out at the time the eggs are transferred from an incubator to a hatcher.

18. A method according to claim 13, wherein said plurality of bird eggs are chicken eggs.

* * * * *